(12) United States Patent
Ramare

(10) Patent No.: US 7,569,068 B2
(45) Date of Patent: Aug. 4, 2009

(54) SPINAL OSTEOSYNTHESIS SYSTEM

(75) Inventor: Stéphane Ramare, Biarritz (FR)

(73) Assignee: Kiscomedica, Saint-Priest (FR)

( * ) Notice: Subject to any disclaimer, the term of this patent is extended or adjusted under 35 U.S.C. 154(b) by 632 days.

(21) Appl. No.: 10/510,178

(22) PCT Filed: Apr. 2, 2003

(86) PCT No.: PCT/FR03/01017

§ 371 (c)(1),
(2), (4) Date: Jun. 30, 2005

(87) PCT Pub. No.: WO03/084415

PCT Pub. Date: Oct. 16, 2003

(65) Prior Publication Data

US 2006/0064088 A1 Mar. 23, 2006

(30) Foreign Application Priority Data

Apr. 4, 2002 (FR) .................................. 02 04181

(51) Int. Cl.
*A61B 17/70* (2006.01)
(52) U.S. Cl. ........................ 606/246; 606/280
(58) Field of Classification Search ............. 606/61, 606/69–73
See application file for complete search history.

(56) References Cited

U.S. PATENT DOCUMENTS

| 3,778,610 | A | * | 12/1973 | Wolf | 362/418 |
|---|---|---|---|---|---|
| 5,092,867 | A | * | 3/1992 | Harms et al. | 606/61 |
| 5,344,422 | A | * | 9/1994 | Frigg | 606/61 |
| 5,382,248 | A | * | 1/1995 | Jacobson et al. | 606/60 |
| 5,501,684 | A | * | 3/1996 | Schlapfer et al. | 606/73 |
| 5,505,731 | A | * | 4/1996 | Tornier | 606/61 |
| 5,569,247 | A |  | 10/1996 | Morrison |  |
| 5,591,166 | A | * | 1/1997 | Bernhardt et al. | 606/61 |
| 5,628,740 | A | * | 5/1997 | Mullane | 606/61 |
| 5,702,394 | A | * | 12/1997 | Henry et al. | 606/61 |
| 5,716,357 | A | * | 2/1998 | Rogozinski | 606/61 |
| 5,735,850 | A | * | 4/1998 | Baumgartner et al. | 606/61 |
| 5,800,435 | A | * | 9/1998 | Errico et al. | 606/61 |
| 6,050,997 | A | * | 4/2000 | Mullane | 606/61 |
| 6,146,383 | A | * | 11/2000 | Studer et al. | 606/61 |

(Continued)

FOREIGN PATENT DOCUMENTS

EP         1 023 873         8/2000

(Continued)

*Primary Examiner*—Eduardo C Robert
*Assistant Examiner*—David Comstock
(74) *Attorney, Agent, or Firm*—Young & Thompson

(57) ABSTRACT

A spinal osteosynthesis system includes at least a pedicular screw (1) with a head (5), a lug (2), a plate (6), elements (10) for fixing the end (4) of the lug on the head (5) including a hemispherical portion (11) integral with the head (5), a hemispherical portion (12) integral with the end (4), the portions being complementary to each other, elements for mutually fixing together the hemispherical portions, and elements (20) for fixing the plate (6) on the end (7) of the lug (2) including a hemispherical part (23) integral with the plate (6), a hemispherical part (24) integral with the end (7), the parts (24) being complementary to each other (23), and elements for mutually fixing together the hemispherical parts (23, 24) when they cooperate inside each other.

3 Claims, 2 Drawing Sheets

U.S. PATENT DOCUMENTS

| | | | |
|---|---|---|---|
| 6,267,765 B1 * | 7/2001 | Taylor et al. | 606/61 |
| 6,273,914 B1 * | 8/2001 | Papas | 623/17.11 |
| 6,379,354 B1 * | 4/2002 | Rogozinski | 606/61 |
| 6,610,062 B2 * | 8/2003 | Bailey et al. | 606/61 |
| 6,626,904 B1 * | 9/2003 | Jammet et al. | 606/61 |
| 6,991,632 B2 * | 1/2006 | Ritland | 606/61 |
| 7,121,755 B2 * | 10/2006 | Schlapfer et al. | 403/77 |
| 7,163,538 B2 * | 1/2007 | Altarac et al. | 606/61 |

FOREIGN PATENT DOCUMENTS

| | | |
|---|---|---|
| FR | 2 780 631 | 1/2000 |
| GB | 38 41 008 | 6/1990 |

* cited by examiner

US 7,569,068 B2

SPINAL OSTEOSYNTHESIS SYSTEM

FIELD OF THE INVENTION

The present invention relates to spinal osteosynthesis systems, which find a particularly advantageous application in holding two optionally-consecutive vertebrae relative to each other, with the aim of carrying out spinal arthrodesis, for example, in a human being in order to suppress, for example, the source of pain generated by a fractured vertebra or in order to avoid the risk of paralysis complications arising from the fracture.

BACKGROUND OF THE INVENTION

Surgeons working in the field of spinal surgery make use in particular of systems that consist essentially of a plate in which an orifice and a slot are formed, and of screws each having a shank with a bone thread terminated by a shoulder head, such screws being suitable for cooperating with the plate so that plate bearing against the vertebrae is held captive between the vertebrae and the shoulder heads of the screws.

Those spinal osteosynthesis systems present drawbacks, in particular because the spinal processes make it difficult to place bone-thread screws in the orifices in the plate so they can be screwed into the vertebral bodies, and do not allow for easy adjustment of the distance between the two segments of vertebrae by the surgeon in order to eliminate the source of pain and bring the segment of the spinal column back to its normal height.

In an attempt to overcome those drawbacks, systems have been developed comprising pedicular screws, lugs, first means for fastening a first end of each lug onto the head of a pedicular screw, at least one plate, and second means for fastening the plate onto the other end of each lug. Nevertheless, those systems are still relatively complex in terms both of putting them in place and of achieving good adjustment to the various distances.

OBJECT OF THE INVENTION

The present invention therefore aims to provide a spinal osteosynthesis system that enables the above-mentioned drawbacks of the prior art to be mitigated to a large extent.

SUMMARY OF THE INVENTION

More precisely, the present invention provides a spinal osteosynthesis system comprising at least one pedicular screw with a head, a lug, first means for fastening a first end of the lug to the head of the pedicular screw, a plate, and second means for fastening the plate to the second end of the lug, characterized by the fact that first means for fastening the first end of the lug onto the pedicular screw head comprise:

a first portion of hemispherical shape secured to the head of the pedicular screw;

a second portion of hemispherical shape secured to the first end of the lug, this second hemispherical portion being complementary to the first hemispherical portion; and fastener means for fastening together the first and second hemispherical portions when they cooperate one in the other with a common first center of curvature, and by the fact that the second fastener means for fastening the plate on the second end of the lug comprise:

a third portion of hemispherical shape secured to the plate, a fourth portion of hemispherical shape secured to the second end of the lug, this fourth hemispherical portion being complementary to the third hemispherical portion, and fastener means for fastening together the third and fourth hemispherical portions when they cooperate one in the other with a common second center of curvature.

BRIEF DESCRIPTION OF THE DRAWINGS

Other features and advantages of the invention appear from the following description of the accompanying drawings given by way of non-limiting illustration, in which.

It is specified that, in the figures, the same references refer to the same elements, in whichever figure they appear and however the elements are shown. Likewise, in any of the figures, if elements do not have specific references, their references can easily be found by referring to another figure.

The Applicant also wishes to make it clear that the figures show only one embodiment of the invention, and that other embodiments can also exist which satisfy the definition of the invention.

Moreover, the Applicant makes it clear that when, according to the definition of the invention, the subject matter of the invention comprises "at least one" element with a given function, the embodiment described may comprise a plurality of such elements.

In addition, the Applicant makes it clear that if the embodiment of the invention as illustrated comprises a plurality of elements of identical function and if, in the description, it is not specified that the invention must necessarily comprise some specific number of such elements, then the invention may be defined as comprising "at least one" such element.

DETAILED DESCRIPTION OF THE INVENTION

Figure 1:
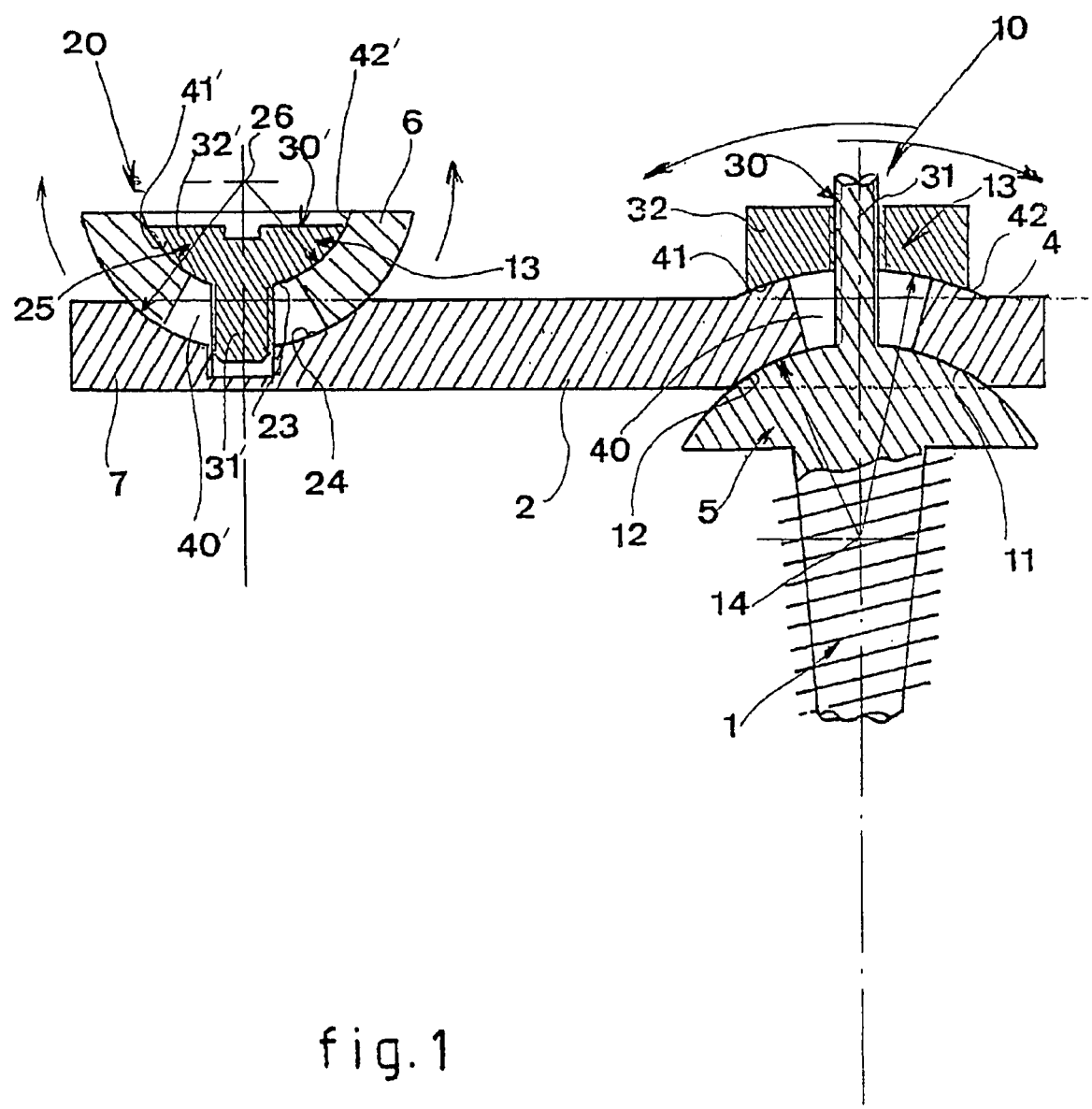
FIG. 1 is a cross section of a portion of an embodiment of the spinal osteosynthesis system of the invention, this section being in the plane referenced P in FIG. 2.

With reference to FIG. 1, the spinal osteosynthesis system comprises at least one pedicular screw 1 with a head 5, a lug 2, first means 10 for fastening the first end 4 of the lug 2 to the head 5 of the pedicular screw, a plate 6, and second means 20 for fastening the plate 6 to the second end 7 of the lug 2.

According to a characteristic of the invention, the first means 10 for fastening the first end 4 of the lug 2 to the head 5 of the pedicular screw comprise a first portion 11 of hemispherical shape secured to the head 5 of the pedicular screw 1, a second portion 12 of hemispherical shape secured to the first end 4 of the lug 2, this second hemispherical portion 12 being complementary to the first hemispherical portion 11, and fastener means 13 for fastening together the first and second hemispherical portions 11, 12, when they cooperate one in the other with a common first center of curvature 14.

With reference to the second means 20 for fastening the plate 6 onto the second end 7 of the lug 2, they comprise a third portion 23 of hemispherical shape secured to the plate 6, a fourth portion 24 of hemispherical shape secured to the second end 7 of the lug 2, this fourth hemispherical portion 24 being complementary to the third hemispherical portion 23, and fastener means 25 for fastening together the third and fourth hemispherical portions 23, 24, when they cooperate one in the other with a common second center of curvature 26.

In a particularly advantageous embodiment, the fastener means 13 and/or 25 defined above include a fastening screw 30 made up of a threaded shank 31 and a screwing head 32, and means for assembling said fastening screw 30 in cooperation with the two hemispherical portions 11-12 and/or 23-24 so that it sandwiches one of the two portions between the other portion and the screwing head 32.

Preferably, the means for assembling the fastening screw 30, in cooperation with the two hemispherical portions for sandwiching one of the two portions between the other portion and the screwing head, are constituted, like the means 13 shown on the right hand side of FIG. 1, by the fact that the threaded shank 31 is secured to the hemispherical portion sandwiching the other hemispherical portion and goes through said other hemispherical portion via a hole 40 of section greater than that of the said threaded shank 31, the screwing head 32 then being screwed onto the threaded shank 31, the two faces 41, 42 of the screwing head 32 and of the hemispherical portion that come into contact with each other being of complementary hemispherical shapes and with centers of curvature that coincide substantially with the center of curvature 14 of the hemispherical portions cooperating one in the other.

Advantageously, when the first and second hemispherical portions 11, 12 are respectively convex and concave, the two faces 41, 42 of the screwing head 32 and of the hemispherical portion that come into contact with each other are respectively concave and convex, as shown on the right hand side of FIG. 1.

Nevertheless, in another embodiment, the means for assembling the fastening screw 30' in cooperation with the two hemispherical portions for sandwiching one of the two portions between the other portion and the screwing head 32' are constituted, like the means 13 shown on the left hand side of FIG. 1, by the fact that the threaded shank 31' is screwed into the hemispherical portion sandwiching the other portion and goes through the other portion via a hole 40' of section greater than that of the threaded shank 31', the screwing head 32' being secured to the threaded shank 31', the two faces 41', 42' of the screwing head 32' and of the hemispherical portion that come into contact with each other being of complementary hemispherical shapes and with centers of curvature that coincide substantially with the center of curvature 26 of the hemispherical portions cooperating one in the other.

Advantageously, when the third and fourth hemispherical portions 23, 24 are respectively convex and concave, the two faces 41', 42' of the screwing head 32' and of the hemispherical portion that come into contact with each other are convex and concave respectively, as shown on the left hand side of FIG. 1.

In terms of its essential definition, the above-described embodiment of the spinal osteosynthesis system of the invention comprises at least one pedicular screw 1, one lug 2 per pedicular screw, and at least one plate 6. Nevertheless, in practice, it is clear that such a system will be made in the manner shown in FIG. 2, for example.

Figure 2:
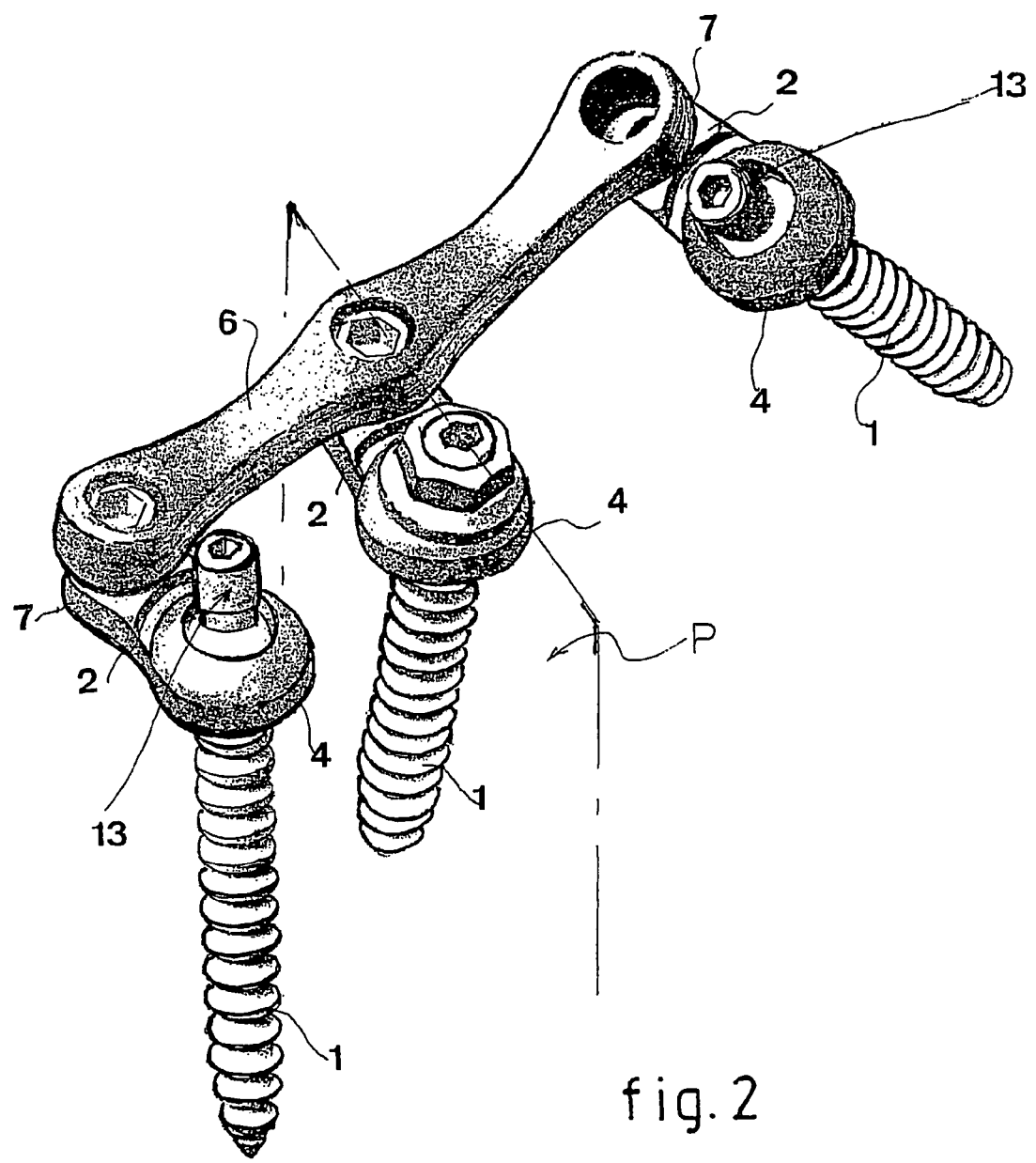
FIG. 2 is a perspective view of an embodiment of the spinal osteosynthesis system in compliance with FIG. 1.

In the embodiment of FIG. 2, the system comprises a plurality of pedicular screws 1, there being three of them in FIG. 2, one lug per pedicular screw, and one plate 6, which plate 6 includes at least as many third hemispherical portions 23 as there are lugs 2, and hence as there are pedicular screws.

Nevertheless, in other possible embodiments, the system may include a plurality of lugs per pedicular screw, the first ends of the lugs being superposed one on another, so that they can turn relative to one another.

In order to implant a spinal osteosynthesis system such as that shown in FIG. 2, the surgeon begins by screwing the three pedicular screws 1 into the vertebral pedicles. In view of the difficulty of implanting such screws, it is impossible to ensure that they are accurately parallel to one another and that the heads are in perfect alignment along the same straight line. Under such conditions, it is practically impossible to place a plate on the three screw heads, since the plate is generally rectilinear.

With the spinal osteosynthesis system of the invention, once the pedicular screws have been screwed firmly into the pedicles, the surgeon places one lug 2 on each pedicular screw in such a way that the first and second hemispherical portions 11, 12 are superposed as shown in FIGS. 1 and 2, the threaded shank 31 going through the hole 40 and the screwing head 32 being screwed on loosely.

The surgeon then assembles the plate 6 to cooperate with the second ends 7 of the lugs 2 so that the third and fourth hemispherical portions 23, 24 cooperate one in the other and then screws the threaded shanks 31 loosely into the lugs 2 (left hand side of FIG. 1).

Using a well-known ancillary instrument, the surgeon distracts the vertebrae so that they take up their desired relative position. While the vertebrae are moving relative to one another, the lugs 2 and the plate 6 also move relative to one another and, because of the hemispherical portions 11-12, 23-24, they are always in the desire optimum position.

The surgeon then locks the hemispherical portions by means of fastening screws 30 and can remove the distraction ancillary.

With the spinal osteosynthesis system of the based on the invention having structural characteristics as described above, it is thus very easy to position the plate 6 relative to the pedicular screws 1, given that each lug 2, can move within a cone around the head 5 of the pedicular screw with which it is associated, and that the plate 6, can move within a cone around the second end 7 of the lug 2.

The description above shows the main advantages of the spinal osteosynthesis system of the invention. Namely: the pedicular screws 1 can be implanted relatively independently of one another, the plate 6 can always be connected to the pedicular screws whatever their relative positions and, since it is positioned laterally relative to the pedicular screws, it can be put in place without being obstructed by spinous processes.

The invention claimed is:

1. A spinal osteosynthesis system comprising at least one pedicular screw with a head, a lug, first means for fastening a first end of the lug to the head of the pedicular screw, a plate and second means for fixing the plate to a second end of the lug, said first means for fastening the first end of the lug onto the pedicular screw head comprises:
  a first portion of hemispherical shape secured to the head of the pedicular screw;
  a second portion of hemispherical shape secured to the first end of the lug, said second hemispherical portion being complementary to the first hemispherical portion; and
  fastener means for fastening together the first and second hemispherical portions to cooperate one in the other with a common first center of curvature, said fastener means for fastening together the first and second hemispherical portions comprising a fastening screw made up of a threaded shank and a screwing head, and means for assembling said fastening screw in cooperation with the first and second hemispherical portions so as to sandwich one of the first and second hemispherical portions between the other of the first and second hemispherical portions and the screwing head, said means for assembling the fastening screw are configured so that the threaded shank is secured to the one hemispherical portion sandwiching the other hemispherical portion and goes through said other hemispherical portion via a hole of section greater than that of said threaded shank, the screwing head being screwed onto said threaded shank, faces of the screwing head and of a hemispherical portion that comes into contact with the screwing head being of complementary hemispherical shapes and with centers of curvature that coincide substantially with the centers of curvature of the hemispherical portions, and the second fastener means for fastening the plate onto the second end of the lug comprise:

a third portion of hemispherical shape secured to the plate, a fourth portion of hemispherical shape secured to the second end of the lug, said fourth hemispherical portion being complementary to the third hemispherical portion, and fastener means for fastening together the third and fourth hemispherical portions to cooperate one in the other with a common second center of curvature.

2. The system according to claim 1, wherein the first and second hemispherical portions are respectively convex and concave, and the faces of the screwing head and of the hemispherical portion that come into contact with the screwing head are respectively concave and convex.

3. The system according to claim 1, wherein the third and fourth hemispherical portions are respectively convex and concave, faces of the fastener means for fastening together the third and fourth hemispherical portions are respectively convex and concave.

* * * * *